United States Patent [19]
Banez

[11] 4,022,194
[45] May 10, 1977

[54] FIBEROPTIC SCOPE SHIELD AND INSTRUMENT HOLDER

[76] Inventor: Armin V. Banez, 510 Gypsy Lane, Youngstown, Ohio 44505

[22] Filed: June 2, 1975

[21] Appl. No.: 582,994

[52] U.S. Cl. ............................................. 128/4
[51] Int. Cl.² ..................................... A61B 1/00
[58] Field of Search ........................... 128/3–11, 128/23, 17; 350/96 B; 248/443

[56] References Cited
UNITED STATES PATENTS

| | | | |
|---|---|---|---|
| 2,470,013 | 5/1949 | Bhajekar | 128/4 |
| 3,044,461 | 7/1962 | Murdock | 128/4 |
| 3,067,648 | 12/1962 | Cohen | 128/4 |

FOREIGN PATENTS OR APPLICATIONS 716,395   12/1931   France ........................... 128/7

Primary Examiner—Robert W. Michell
Assistant Examiner—Henry S. Layton
Attorney, Agent, or Firm—Webster B. Harpman

[57] ABSTRACT

A shield and instrument holder for use with a fiberoptic scope such as those designed for proctologic use positions an apertured shield portion transversely of the eye piece of the fiberoptic scope, which eye piece extends through the aperture to secure the shield and provides a right angular extension in spaced parallel relation to the fiberoptic scope adjacent the eye piece with means thereon for detachably holding various instruments in convenient relation thereto.

6 Claims, 3 Drawing Figures

FIBEROPTIC SCOPE SHIELD AND INSTRUMENT HOLDER

BACKGROUND OF THE INVENTION

1. Field of the Invention

This invention relates to fiberoptic scopes such as used for examining body cavities and the like and more particularly to a shield mounted on the scope in protective relation to the user thereof and at the same time providing a convenient instrument holder.

2. Description of the Prior Art

U.S. Pat. No. 3,044,461 discloses a window-like member pivoted to a procto-sigmoidoscope so that it can be moved to a position covering the open end of the scope or allowed to depend therebelow. A somewhat similar arrangement is seen in U.S. Pat. No. 3,067,648 wherein lenses are arranged in a rotatable manner relative to a scope and U.S. Pat. No. 2,470,013 shows a number of attachments on an endoscope handle.

This invention provides a positive shield structure around and about and particularly below the eye piece of a fiberoptic scope together with a convenient instrument holder extending therefrom and adjacent the body of the scope on which the shield is positioned.

SUMMARY OF THE INVENTION

A fiberoptic scope shield and instrument holder comprises a rectangular shield apertured in its upper central portion so that it can be attached thereby to the eye piece of a fiberoptic scope. The shield includes a transversely positioned trough in which absorbent material can be positioned to contain fluids intercepted by the shield together with an extension, a portion of which also engages the fiberoptic scope and includes transverse configurations particularly adapted for the temporary reception and holding of various instruments.

DESCRIPTION OF THE PREFERRED EMBODIMENT

Figure 1:
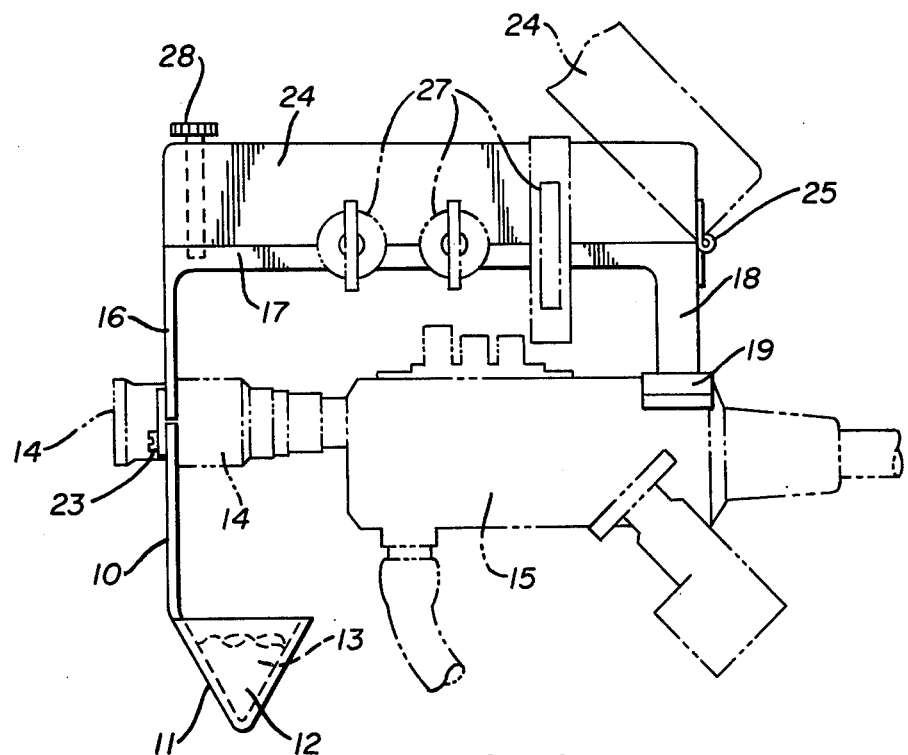
FIG. 1 is a side elevation of the fiberoptic scope shield and instrument holder in position on a fiberoptic scope, portions of which are broken away.

In the form of the invention chosen for illustration herein and as seen in FIG. 1 of the drawings, the fiberoptic scope shield and instrument holder comprises a rectangular shield 10 the lower transverse portion of which is formed in a cross sectionally V-shaped trough 11 having end closures 12 and preferably obtaining absorbent material such as cotton 13.

The rectangular shield 10 is apertured in its upper central portion for the reception of an eye piece 14 of a fiberoptic scope 15 which may be one used for proctologic examination or alternately a gastroscope, bronchoscope or the like. The upper transverse edge of the rectangular shield 10 is detachably secured to a depending portion 16 of a right angularly disposed elongated instrument holder portion 17, the opposite end of which has a downwardly depending leg 18 terminating in a bracket 19 shaped to engage and rest upon the body 15 of the fiberoptic scope at a location spaced with respect to the eye piece 14 thereof.

The aperture defined in the upper central portion of the rectangular shield 10 of the device is formed by registering oppositely disposed notches 20 and 21, each of which are half circular in configuration so as to form the aperture which registers with the eye piece 14 of the fiberoptic scope and mounts the device of the invention thereon.

The depending portion 16 of the elongated instrument holder 17 is of the same width as the shield 10 and has a pair of depending tabs 22 thereon, each of which is apertured for the reception of a fastener 23 which are also threadably engaged in threaded openings in the shield 10, thus the shield 10 is formed of the principal rectangular portion 10 and the lower depending portion 16 of the instrument holder 17.

Alternately it will occur to those skilled in the art that these parts of the device can be integral with an aperture formed therein and usable when the eye piece of a fiberoptic scope or the like is separable so that it can be positioned through the aperture and reassembled to secure the shield and instrument holder thereto.

Figure 2:
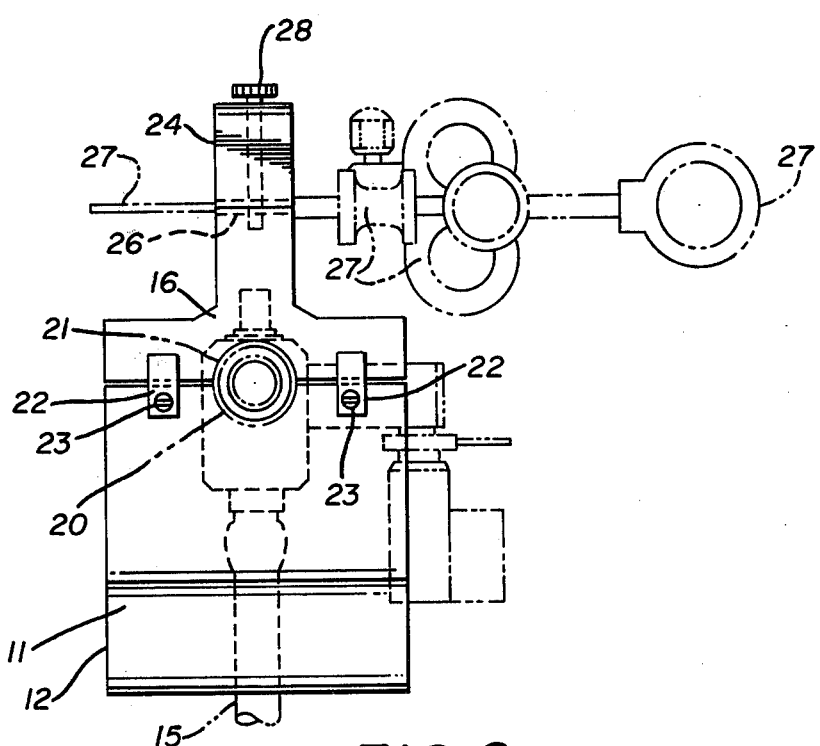
FIG. 2 is an end elevation taken on the left end of FIG. 1.

The two part detachable construction of the shield 10 and the depending portion 16 of the instrument holder of the preferred embodiment of the invention are best illustrated in FIG. 2 of the drawings.

Figure 3:
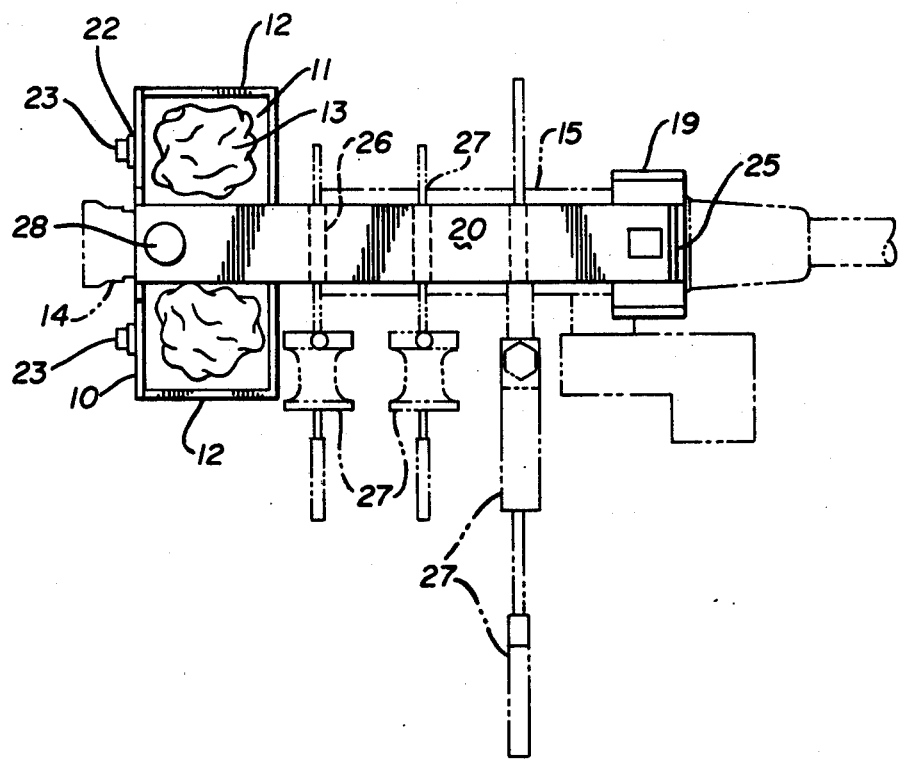
FIG. 3 is a top plan view of the device of the invention.

By referring now to FIGS. 1, 2 and 3 of the drawings, it will be seen that the elongated portion 17 of the instrument holder portion of the invention has a secondary elongated portion 24 positioned on the upper surface thereof and hinged in relation thereto by a hinge 25. Both the elongated portion 17 of the instrument holder portion and the secondary elongated portion 24 have oppositely disposed matching configurations 26 as shown in FIGS. 2 and 3 in broken line illustration by means of which a plurality of instruments 27 may be clampingly held by the instrument holder in convenient relation to the fiberoptic scope 15.

The secondary elongated portion 24 of the instrument holder part of the device is provided with a thumb screw 28 positioned in a vertical opening in the end therof opposite the hinge 25 and for registry with a threaded opening in the elongated portion 17. This enables the instrument holder portion of the device to securely hold and/or position the instruments 27 at the option of the user.

It will thus occur to those skilled in the art that the shield and instrument holder disclosed herein for attachment to and use with fiberoptic scopes protects the user from the accidental discharge of body fluids and the like which sometimes occur during the course of an examination of a body cavity. Such fluids as may be intercepted by the shield 10 are directed into the V-shaped trough 11 at the lower edge thereof and retained in the absorbant cotton material preferably disposed therein.

Although but one embodiment of the present invention has been illustrated and described, it will be apparent to those skilled in the art that various changes and modifications may be made therein without departing from the spirit of the invention.

Having thus described my invention what I claim is:

1. A shield and instrument holder for use with a fiberoptic scope or the like having a body and an extending eye piece and comprising a substantially sized shield portion apertured inwardly of its edges for the reception of the eye piece and arranged to engage said eye piece so as to hold said shield and instrument holder thereon in a position to shield a user's face, an extension on said shield portion and means on said extension for detachably engaging at least one instrument so as to position the same adjacent said scope in spaced relation to said eye piece.

2. The shield and instrument holder of claim 1 and wherein means is formed on said shield for receiving and retaining fluids directed against said shield.

3. The shield and instrument holder of claim 1 and wherein said shield portion is vertically disposed and said extension on said shield portion is positioned on the upper edge thereof and includes a right angular portion and wherein said means for detachably engaging said instrument is positioned on said right angular extension.

4. The shield and instrument holder of claim 1 and wherein said shield portion is vertically disposed and comprises a lower rectangular section and an upper section of comparable width and means detachably joining said sections and wherein said aperture is defined by half circular registering notches in said upper and lower sections.

5. The shield and instrument holder of claim 1 and wherein the extension of the shield is positioned upwardly thereof and includes a right angular portion and wherein said means for detachably engaging at least one instrument comprises a second right angular portion removably affixed to said first mentioned right angular portion with said first and second right angular portions having matching and registering configurations between which said instrument may be positioned.

6. The shield and instrument holder of claim 1 and wherein the extension of the shield includes a right angular portion having a secondary portion hingedly affixed thereto and means for clamping the secondary portion to the right angular portion and wherein the right angular portion has a downturned end engagable with said fiberoptic scope so as to support the same in spaced relation thereto.

* * * * *